United States Patent
Kozacheck et al.

(10) Patent No.: US 9,931,284 B2
(45) Date of Patent: Apr. 3, 2018

(54) METHOD OF REMOVING POLYMERIZED COATINGS FOR HUMAN NAILS, POLYMERIZED COATING FOR HUMAN NAILS HAVING IMPROVED REMOVABILITY, AND TWO PACKAGE SYSTEM

(71) Applicant: MYCONE DENTAL SUPPLY COMPANY, INC., Gibbstown, NJ (US)

(72) Inventors: Joseph Kozacheck, Newtown Square, PA (US); George Lein, Elkton, MD (US); Larry Steffier, Cherry Hill, NJ (US)

(73) Assignee: MYCONE DENTAL SUPPLY COMPANY, INC., Gibbstown, NJ (US)

( * ) Notice: Subject to any disclaimer, the term of this patent is extended or adjusted under 35 U.S.C. 154(b) by 197 days.

(21) Appl. No.: 14/776,414

(22) PCT Filed: Mar. 14, 2014

(86) PCT No.: PCT/US2014/028427
§ 371 (c)(1),
(2) Date: Sep. 14, 2015

(87) PCT Pub. No.: WO2014/152964
PCT Pub. Date: Sep. 25, 2014

(65) Prior Publication Data
US 2016/0030310 A1 Feb. 4, 2016

Related U.S. Application Data

(60) Provisional application No. 61/782,648, filed on Mar. 14, 2013, provisional application No. 61/872,088, filed on Aug. 30, 2013.

(51) Int. Cl.
| | |
|---|---|
| *A61K 8/34* | (2006.01) |
| *A61K 8/81* | (2006.01) |
| *A61Q 3/02* | (2006.01) |
| *A61Q 3/04* | (2006.01) |
| *A61K 8/35* | (2006.01) |
| *A45D 29/18* | (2006.01) |

(52) U.S. Cl.
CPC ............ *A61K 8/34* (2013.01); *A45D 29/18* (2013.01); *A61K 8/35* (2013.01); *A61K 8/8152* (2013.01); *A61Q 3/02* (2013.01); *A61Q 3/04* (2013.01); *A61K 2800/81* (2013.01); *A61K 2800/88* (2013.01)

(58) Field of Classification Search
CPC .......... A61K 8/34; A61K 8/8152; A61K 8/35; A61K 2800/81; A61K 2800/88; A61Q 3/02; A61Q 3/04; A45D 29/18
See application file for complete search history.

(56) References Cited

U.S. PATENT DOCUMENTS

| | | | |
|---|---|---|---|
| 3,928,113 A | 12/1975 | Rosenberg | |
| 5,077,038 A | 12/1991 | Hofmann | |
| 5,118,495 A | 6/1992 | Nafziger et al. | |
| 5,582,333 A * | 12/1996 | Bennett | A45D 29/007 222/546 |
| 5,985,951 A | 11/1999 | Cook | |
| 2004/0185026 A1 | 9/2004 | Pantini | |
| 2011/0182838 A1 | 7/2011 | Vu et al. | |
| 2011/0226271 A1 | 9/2011 | Raney et al. | |
| 2013/0034512 A1 | 2/2013 | Kozacheck et al. | |

FOREIGN PATENT DOCUMENTS

| | | | | |
|---|---|---|---|---|
| WO | WO2011/130362 | * | 10/2011 | ............ A61K 8/37 |
| WO | 2013028862 A1 | | 2/2013 | |

OTHER PUBLICATIONS

The Communication and the extended European search report issued by EPO dated Dec. 21, 2015 for corresponding EP application No. 14767785.0.
International Search Report and Written Opinion issued by KIPO(ISA) dated Jul. 24, 2014 for International patent application No. PCT/US2014/028427.
International Preliminary Report on Patentability and Written Opinion of the International Preliminary Examining Authority issued by USPTO(IPEA) dated Jun. 24, 2015 for International patent application No. PCT/US2014/028427.

* cited by examiner

*Primary Examiner* — Trevor Love
(74) *Attorney, Agent, or Firm* — Michael B. Fein; Eckert Seamans Cherin & Mellott, LLC

(57) ABSTRACT

A method for removing a radiation-polymerized cosmetic coating from nails comprising applying a solvent system comprising a hydroxyl-containing solvent and a non-hydroxyl-containing solvent to a polymerized nail coating. A two package system comprising a first package comprising polymerizable nail coating composition comprising a (meth) acrylic oligomer, (meth)acrylic monomer, or a mixture of a (meth)acrylic oligomer and a (meth)acrylic monomer, and a photoinitiator, wherein the oligomer or monomer has an acidic or basic ionizable group and a second package comprising a solvent system for removing the polymerizable nail coating composition after it has been applied to a nail and radiation cured, the solvent system comprising a hydroxyl-containing solvent and a non-hydroxyl-containing solvent. A radiation-curable coating composition for human nails is also disclosed.

2 Claims, No Drawings

METHOD OF REMOVING POLYMERIZED COATINGS FOR HUMAN NAILS, POLYMERIZED COATING FOR HUMAN NAILS HAVING IMPROVED REMOVABILITY, AND TWO PACKAGE SYSTEM

CROSS-REFERENCE TO RELATED APPLICATIONS

This application is the U.S. national stage of PCT/US2014/028427 filed Mar. 14, 2014, which claims priority from Provisional Application No. 61/782,468, filed Mar. 14, 2013, and Provisional Application No. 61/872,088 filed Aug. 30, 2013, all of which are hereby incorporated by reference.

BACKGROUND OF THE INVENTION

This invention relates to polymerized cosmetic coatings for human nails and particularly to improved removability thereof.

Radiation curable cosmetic coatings for human nails are typically applied in professional nail salons wherein nail technicians apply a gel coating to fingernails or toenails and expose the coating to ultraviolet light radiation to cure the coating, resulting in a far more durable coating than can be achieved with solvent based nail polishes. While solvent-based nail polishes are easily removed with solvent such as acetone, polymerized cosmetic coatings are designed to be very durable and often are not easily removable in comparison to air dryed nail varnishes. Various solutions to the problem of removability of polymerized cosmetic coatings for human nails have been proposed, for example Rosenberg in U.S. Pat. No. 3,928,113 proposed applying a basecoat comprising a water-soluble or water-swellable polymer in a solvent system followed by application and then curing of a photocurable nail lacquer composition. Thong, et al., U.S. Pat. Publ. 2011/0182838, disclosed polymerized cosmetic coatings for natural and artificial nails having improved removability with solvents comprising a reactive (meth) acrylate, a reactive urethane (meth)acrylate, a reactive polypropylene glycol monomethacrylate, a polymethylmethacrylate-polymethacrylic acid copolymer, a pyromellitic dianhydride glyceryl dimethacrylate, a non-reactive solvent-dissolvable polymer, a non-reactive solvent which cures under radiation to an acrylic thermoset having voids which contain a solvent-dissolvable polymer. There are problems with the Rosenberg, Thong, et al., and other prior art approaches to this problem which the present invention solves. Rosenberg, for example, fails due to high water sensitivity since the base coat is not resistant to water and causes lifting of the entire coating system when exposed to water. Neither reference discloses acids or bases in the solvent system used for removal.

SUMMARY OF THE INVENTION

The present invention comprises, in one aspect, a method for removing a radiation polymerized cosmetic coating from nails, wherein the coating comprises a compound containing an acidic or basic group or a salt and is not removable by water, comprising applying a solvent system comprising an organic hydroxyl-containing solvent to the polymerized cosmetic coating.

DETAILED DESCRIPTION

In some embodiments of the invention the solvent system also comprises a non-hydroxyl-containing solvent. In some embodiments of the invention the solvent system comprises a mixture of water and a water soluble organic solvent.

In some embodiments of the invention the solvent system comprises a compound containing an acidic group, a basic group or a salt and a hydroxyl containing solvent.

In some embodiments of the invention the solvent system comprises a compound containing an acidic group, a basic group or a salt, a hydroxyl containing solvent and a non-hydroxyl containing solvent.

In some embodiments of the invention the solvent system comprises a compound containing an acidic group, a basic group or a salt and a non-hydroxyl containing solvent.

In some embodiments of the invention the solvent system comprises a compound containing an acidic group, a basic group or a salt and a mixture of water and a water soluble solvent.

Preferred hydroxyl-containing solvents are methanol, ethanol, and isopropanol, optionally diluted with water. Ethanol is an especially preferred hydroxyl-containing solvent. Preferred non-hydroxyl solvents, when present, are acetone and ethyl acetate.

In some embodiments hydroxyl-containing solvents and one or more non-hydroxyl containing solvents such as acetone are mixed and act to remove a polymerized cosmetic coating more effectively than acetone alone.

In some embodiments water and one or more non-hydroxyl containing solvents such as acetone are mixed and act to remove a polymerized cosmetic coating more effectively than acetone alone.

In certain embodiments the solvent system comprises a compound containing a counter-ion to an ionic or ionizable group present in the polymerized cosmetic coating.

In some embodiments the radiation cured coating compositions comprise reactive oligomers or polymers which contain acidic, basic or cationic groups wherein the coating can be removed with non-hydroxyl containing solvents. The oligomers and polymers contain monomeric segments and are made via anionic, cationic, radical or condensation polymerization methods wherein at least 5 monomer units are included in the final material. Preferred oligomers and polymers have at least 20 monomeric units in the final material. The materials contain vinyl groups which can be incorporated into the film upon radiation curing or the coating. (Meth)acrylic vinyl groups are preferred. By (meth) acrylic we mean both acrylic and methacrylic vinyl groups. It is expected that the use of these materials in the coating improves overall adhesion of the coating to the nail surface.

In certain embodiments the solvent system comprises a compound containing a basic or acidic group or salt thereof. The basic group can be, for example, an amine, especially when the polymerized cosmetic coating contains an acidic group in a neutral or ionized form which is present in certain embodiments. For example, the solvent system can comprise triethanolamine or its salt and the polymerized cosmetic coating can contain an acidic group such as a carboxylic acid, sulfonic acid, or phosphorous based acid or salt thereof.

In other embodiments the solvent system comprises a compound containing an acidic group or salt of an acidic group and the polymerized cosmetic coating contains a basic group or a cation. For example the solvent system can comprise an acidic group such as a carboxylic acid, sulfonic acid, phosphoric acid, hydrochloric acid, acetic acid and/or citric acid or a salt of the acid and the polymerized cosmetic coating can contain a basic group such as an amine group, an amine salt, a quaternary ammonium group or a phosphonium salt. In other embodiments the solvent system comprises a compound containing an acidic group or salt of an acidic group and a non-hydroxyl containing solvent.

In other embodiments, a polymerizable coating containing acidic, basic or cationic groups can be applied to the nail or to another cured or dried coating and left uncured or only partially cured. In this embodiment another coating which may or may not contain acidic, basic or cationic groups is then applied and both coatings are then cured.

In another aspect, the invention comprises a two package system comprising a first package comprising radiation polymerizable nail coating composition comprising a photoinitiator and a (meth)acrylic oligomer or polymer, (meth)acrylic monomer, or a mixture of a (meth)acrylic oligomer or polymer and a (meth)acrylic monomer, wherein the oligomer or monomer has an acidic or basic ionizable group, a salt of that group, or a cationic group. The first package can also comprise a non-polymerizable additive having an acidic or basic ionizable group or a salt. The second package comprises a solvent system for removing the polymerizable nail coating composition after it has been applied to a nail and radiation cured, the solvent system comprising the above-described solvent system.

The oligomer, polymer, monomer, and/or additives in the polymerizable coating composition can have an acidic or basic or cationic group or a salt of the acidic or basic group, in which case the second package can comprise a solvent system for removing the polymerizable nail coating composition after it has been applied to a nail and radiation cured, the solvent system comprising a compound which can serve to neutralize or act as a counterion to an acidic, basic or cationic group. The acidic group can be a carboxyl, sulfonic, or phosphorous acid based group and the basic group can be an amine. The cationic group can, for example be a quaternary ammonium group.

The acidic or basic group or salt can be incorporated into the polymerizable coating composition in several ways. Exemplary, but not limiting examples include incorporation of monomers containing acidic or basic groups or salts thereof.

Examples of polymerizable, unsaturated monomers useful in the invention include acrylic acid, methacrylic acid, styrene sulfonic acid, maleic acid, monoesters of maleic acid, fumaric acid, monoesters of fumaric acid, dimethylamino ethyl acrylate, dimethyl amino ethyl methacrylate, dimethyl amino propyl acrylate, dimethyl amino propyl methacrylate, methacryloyl ethyl betaine, 2-acrylamido-2-methylpropanesulfonic acid, 2-(Acryloyloxy)ethyl trimethylammonium salts, acrylamidopropyltrimmonium salts, N-(3-dimethylaminopropyl)-2-propenamide, itaconic acid, monoesters of itaconic acid, diethyl amino ethyl acrylate, diethyl amino ethyl methacrylate, vinyl pyridine, aminoethyl acrylate, amino ethyl methacrylate, amino styrene, dimethyl amino styrene, crotonic acid, phosphoethyl (meth) acrylate, salts of dially dimethyl ammonium monomer, N-tolylglycine glycidylmethacrylate, hydroxyalkyl (meth) acrylate and glycerol dimethacrylate adducts of anhydrides including anhydrides of succinic, maleic, phthalic, trimellitic, and pryromellitic acids.

Non-reactive polymers and oligomers which are made from these monomers are also useful in the invention. These materials may be homopolymers of these monomers or copolymers of one or more of these monomers with other monomers. A wide variety of other monomers may be used to form copolymers from the materials above. In general these polymers and oligomers are formed using radical polymerization methods.

Other non-reactive polymers containing acidic or basic groups or salts are also useful in the radiation curable coating compositions invention. Cellulosic materials containing carboxyl groups may be incorporated. Condensation polymers such polyesters, polyurethanes, polyamides and polyureas or polymers containing mixtures of ester, urethane, amide and urea groups may also be incorporated into the coating. For example polyurethanes incorporating acid groups are described in U.S. Pat. No. 3,412,054. Polyesters containing acid groups can be prepared, for example, by condensation of diacids with diols using an excess of diacid to yield acidic end groups. Polyamides with basic or acidic groups can be prepared by condensation of diamines with diacids. Varying the ratio of diacid to diamine allows control of whether the polymer contains residual acidic or basic groups. Residual amine groups can be converted to quaternary ammonium salts if desired. Polymers made by ring opening polymerization such as polyethers made from ethylene oxide, polypropylene oxide or tetrahydrofuran can be made containing, for example, basic groups or salts by including aziridines in the polymerization or using amines as the initial reactant to form the polymer. These or other common methods can be used to include acidic or basic groups or salts into the oligomers or polymers useful in the coating compositions of the invention.

Reactive oligomers containing acidic or basic groups or salts are also useful in the invention. These oligomers can be made by conversion of the non-reactive polymers and oligomers listed above to reactive polymers by a variety of know methods. For example, reactive (meth)acrylic polymers containing acid groups can be prepared by including hydroxyl containing monomers in the polymeric structure followed by reaction of the hydroxyl units with diisocyanates and hydroxyl containing (meth)acrylic monomers or by reaction of the hydroxyl units with (meth)acrylic isocyanates. Reactive urethanes containing acidic groups can be prepared by the formation of iscoyanate terminated prepolymers containing acidic groups, for example by the inclusion of hydroxyl containing materials containing carboxyl radicals, for example, 2-carboxyl, 1,3 dihydroxy propane in the prepolymer followed by reaction of the prepolymer with hydroxyl containing (meth)acrylic monomers. Reactive polyethers containing basic groups can be prepared by reaction of epoxides and aziridines followed by reaction with (meth)acrylic monomers containing acidic groups reaction of the epoxides with (meth)acrylic monomers containing acidic groups. Many other methods exist for forming reactive oligomers and polymers containing acidic or basic groups or salts which are useful in the invention. Examples of monomers, reactive oligomers, non reactive oligomers and polymers or other additives useful in the invention include those containing carboxylic acid, sulfonic acid, and phosphorous based acid groups as well as basic groups such as amino groups, and salts of these acidic and basic groups. Monomers, reactive oligomers, non-reactive oligomers, polymers and other materials containing quaternary ammonium groups are also useful in the invention.

In some embodiments the oligomer or monomer has an acidic ionizable group from a carboxylic acid, sulfonic acid, phosphorous based acid and the solvent system can comprise an amine compound.

The coatings may also contain monomers and oligomers which are used in the art of radiation curable nail coatings. Examples of other useful monomers include esters and amides of acrylic and methacrylic acid. The esters of acrylic and methacrylic acid are herein termed (meth)acrylic ester. Specific but not limiting examples of mono methyl (meth)

acrylic esters include: methyl (meth)acrylate, ethyl (meth)acrylate hydroxypropyl (meth)acrylate, ethyl (meth)acrylate, butyl (meth)acrylate, hydroxy ethyl (meth)acrylate, butoxyethyl (meth)acrylate, diethylaminoethyl (meth)acrylate, 2-ethylhexyl (meth)acrylate, ethoxyethyl (meth)acrylate, t-butyl aminoethyl (meth)acrylate, methoxyethylene glycol (meth)acrylate, phosphoethyl (meth)acrylate, methoxy propyl (meth)acrylate, methoxy polyethylene glycol(meth)acrylate, phenoxyethylene glycol (meth)acrylate, phenoxypolyethylene glycol (meth)acrylate, 2-hydroxy-3-phenoxypropyl (meth)acrylate, 2-(meth)acryloxyethylsuccinic acid, 2-(meth)acryloylethylphthalic acid, 2-(meth)acryloyloxypropylphthalic acid, stearyl (meth)acrylate, isobornyl (meth)acrylate, 3-chloro-2-hydroxypropyl (meth)acrylate, tetrahydrofurfuryl (meth)acrylate, (meth)acrylamides and allyl monomers. Specific but not limiting examples of difunctional methacryl esters include: 1,4-butane diol di(meth)acrylate, 1,6-hexanediol di(meth)acrylate, 1,9-nonanediol di(meth)acrylate, 1,10-decanediol di(meth)acrylate, neopentyl glycol di(meth)acrylate, 2-methyl-1,8-octane diol di(meth)acrylate, glycerol di(meth)acrylate, ethylene glycol di(meth)acrylate, triethylene glycol di(meth)acrylate, polyethylene glycol di(meth)acrylate, polypropylene glycol di(meth)acrylate, ethoxylated propylene glycol di(meth) acrylate, ethoxylated polypropylene glycol di(meth)acrylate, polyethoxypropoxy di(meth)acrylate, ethoxylated bisphenol A di(meth)acrylate, propoxylated bisphenol A di(meth)acrylate, propoxylated ethoxylated bisphenol A di(meth)acrylate, bisphenol-A glycidyl methacrylate, tricyclodecanedimethanol di(meth)acrylates glycerin di(meth)acrylate, ethoxylated glycerin di(meth)acrylate, bis acrylamides, bis allyl ethers and allyl (meth)acrylates. Examples of tri and or higher (meth)acryloyl esters include trimethylol propane tri(meth)acrylate, ethoxylated glycerin tri(meth) acrylate, ethoxylated trimethylolpropane tri(meth)acrylate, ditrimethylol propane tetra(meth)acrylate, pentaerythritol tri (meth)acrylate, pentaerythritol tetra(meth)acrylate, propoxylated pentaerythritol tetra(meth)acrylate, ethoxylated pentaerythritol tetra(meth)acrylate, dipentaerythritol penta(meth)acrylate, dipentaerythritol hexa(meth)acrylate, and ethoxlated iscyanuric acid tri(meth)acrylates.

Urethane(meth)acrylates, useful in the present invention, have at least two or more acryl or methacryl groups and a urethane group. Examples include: urethanes based on aliphatic, aromatic, polyester, and polyether polyols and aliphatic, aromatic, polyester, and polyether diisocyanates capped with (meth)acrylate end-groups. Isocyanate prepolymers can also be used in place of the polyol-diisocyanate core. Epoxy (meth)acrylates and epoxy urethane (meth) acrylates, useful in the present invention, have at least two or more acryl or methacryl groups and, optionally, a urethane group. Examples include epoxy (meth)acrylates based on aliphatic or aromatic epoxy prepolymers capped with (meth)acrylate end-groups. A aliphatic or aromatic urethane spacer can be optionally inserted between the epoxy and the (meth)acrylate endgroup(s). Acrylated polyester oligomers, useful in the present invention, have at least two or more acryl or methacryl groups and a polyester core. Acrylated polyether oligomers, useful in the present invention, have at least two or more acryl or methacryl groups and a polyether core. Acrylated acrylate oligomers, useful in the present invention, have at least two or more acryl or methacryl groups and a polyacrylic core. These reactive urethanes, epoxies, polyesters, polyethers and acrylics are available from several suppliers including BASF Corporation, Bayer MaterialScience, Bomar Specialties Co, Cognis Corporation, Cytec Industries Inc, DSM NeoResins, Eternal Chemical Co, Ltd, IGM Resins, Rahn AG, Sartomer USA, LLC, and SI Group, Inc.

In addition to the above-described (meth)acrylate-based polymerizable monomers, other polymerizable monomers, oligomers or polymers of monomers which contain at least one free radical polymerizable group in the molecule may be used without any limitations in the curable gel. A compound having at least one free radical polymerizable group includes not only a single component but also a mixture of polymerizable monomers. Thus, combinations of two or more materials containing free radical polymerizable groups may be used in combination.

The gels also contain a photoinitiator. Examples of these include: benzyl ketones, monomeric hydroxyl ketones, polymeric hydroxyl ketones, alpha-amino ketones, acyl phosphine oxides, metallocenes, benzophenone, benzophenone derivatives, and the like. Specific examples include: 1-hydroxy-cyclohexylphenylketone, benzophenone, 2-benzyl-2-(dimethylamino)-1-(4-(4-morphorlinyl)phenyl)-1-butanone, 2-methyl-1-(4-methylthio)phenyl-2-(4-morphorlinyl)-1-propanone, diphenyl-(2,4,6-trimethylbenzoyl) phosphine oxide, phenyl bis(2,4,6-trimethylbenzoyl) phosphine oxide, benzyl-dimethylketal, isopropylthioxanthone, and mixtures thereof.

Photo accelerators such as aliphatic or aromatic amines may also be included in the gel as well as fillers, inhibitors, plasticizers and adhesion promoters.

The coatings may also contain fillers, plasticizers, pigments, dyes, rheology modifiers, and color stabilizers commonly used in the art.

The method for removing a radiation polymerized cosmetic coating from human nails comprises applying a solvent system comprising a hydroxyl-containing solvent to the nail coating wherein the coating comprises an acidic or basic group or a salt and is not removable by water, and allowing the solvent to soak the coating for a short period of time followed by gentle scraping of the nail or wiping with a cloth or washing with water or soap and water. The solvent system can contain both a hydroxyl-containing solvent and a non-hydroxyl-containing solvent. Examples of hydroxyl-containing solvents include methanol, ethanol, and isopropanol, with ethanol being the most preferred. Examples of non-hydroxyl-containing solvents include acetone and ethyl acetate. Mixtures of two or more or either or both solvents are also contemplated.

The UV polymerizable coating composition for human nails can be a specially formulated system comprising an ionic or ionizable group such as an acidic, basic, salt, or cationic group designed especially for easy removability when desired by soaking with a solvent system which comprises hydroxyl as well as non-hydroxyl containing solvent such as acetone, ethyl acetate, and optionally comprising a compound containing a basic or acidic group or a salt. Suitable amines include triethanolamine and suitable acidic compounds are those comprising carboxylic, sulfonic, or phosphoric groups as well as hydrochloric acid.

The polymerized human nail coating can comprise a counter-ion to the acidic or basic compound if present in the solvent system, for example an acidic group when the solvent system comprises an amine or other base, or a basic group such as an amine when the solvent system comprises an acid.

The composition aspect of the invention comprises a two package system or kit comprising a first package comprising polymerizable nail coating composition comprising a (meth)acrylic oligomer, (meth)acrylic monomer, (meth)acrylic polymer or a mixture of a (meth)acrylic oligomer and/or polymer and a (meth)acrylic monomer, optionally an acidic or basic functional additive or salt, and a photoinitiator, wherein the oligomer or monomer has an acidic or basic ionizable group and a second package comprising a solvent system for removing the polymerizable nail coating composition after it has been applied to a nail and radiation cured, the solvent system comprising a hydroxyl-containing solvent and a non-hydroxyl-containing solvent. For example the oligomer, monomer, or polymer can include an acidic ionizable group selected from the group consisting of carboxylic acid, sulfonic acid, or phosphorus based acid or a basic ionizable group such as dimethylaminoethyl (meth)acrylate or dimethylaminopropyl (meth)acrylate, and the solvent system can comprise an amine compound and a hydroxyl-containing compound in the case where the oligomer, monomer or polymer contains an acidic group or an acidic compound in the case where the oligomer, monomer or polymer contains a bsic group. The first package and the second package can be sold separately, of course, and need not be sold as a kit, since in some cases a selection of curable polymer systems and a separate selection of solvent systems can be offered and available to the consumer.

In some embodiments of the UV-curable composition for coating human nails which comprises a photoinitator, a monomer and/or oligomer, and an optional additive, the monomer and/or oligomer and/or optional additive has an ionizable acidic or basic or a cationic group. Such ionizable group is adapted in such embodiments to improve the removability of a coating cured by subjecting the curable composition to UV radiation, the cured coating being removable when soaked with a solvent system comprising a hydroxyl containing solvent and a non-hydroxyl containing solvent containing a compound containing a counterion to the ionizable group in the coating.

EXAMPLES

Example 1—Oligomer Preparation

A reactive oligomer was prepared as follows.

To a resin kettle equipped with a stirrer were charged, under dry air, 0.6 moles of isophorone diisocyanate (IPDI) and 0.160 g of DBDTL and 1.1 g of butylated hydoxy toluene (BHT). Then, 0.6 moles of hydroxyethyl acrylate (HEA) was added over 1 hr followed by addition of 0.30 moles of a 2000 Mw polybutylene glycol diol. After addition the reaction was held at 80° C. until no isocyanate peak remained in the infrared spectrum.

Example 2—Soak Off Results with Acid Containing Oligomers

Materials:

EMA—Ethyl Methacrylate

HEMA—Hydroxymethyl ethyl methacrylate

Sarbox 510E35—An octafunctional acid containing oligomer diluted with ethoxylated trimethyol propane triacrylate Sarbox SB400—An octafunctional acid containing oligomer diluted with PM alcohol TPO—Diphenyl(2,4,6-trimethylbenzoyl)phosphine oxide The following formulations were used:

| Formula 1 | |
|---|---|
| Ingredients | % |
| Oligomer From Example 1 | 20 |
| EMA | 45 |
| Sarbox SB400 | 30 |
| TPO | 5 |
| Total | 100 |

| Formula 2 | |
|---|---|
| Ingredients | % |
| Oligomer From Example 1 | 20 |
| HEMA | 45 |
| Sarbox SB400 | 30 |
| TPO | 5 |
| Total | 100 |

Using a drawdown bar, a 10 mil film of each formulation was applied to a glass slide. The film was then cured for 3 minutes under a standard Ultraviolet Lamp used for curing in the nail industry. After cure the slide was immersed in solvent and the time required for the film to completely release from the glass was measured. Table 1, in which Acetone represents the prior art, gives the results.

TABLE 1

| | Time Required For Soak Off | |
|---|---|---|
| | Solvent | |
| Formula | Acetone | 50:50 Acetone:Methanol |
| 1 | 10 Min | 4 min |
| 2 | >15 min | 5 min |

Example 3—Soak Off Results With Acid-Containing Pre-Coats

In another experiment a primer coat was used which consisted of 20% Sarbox 510E35 dissolved in ethyl acetate. After applying the pre-coat with a nail gel brush, a drawdown was made of formula 3 (components listed in below table).

| Formula 3 | |
|---|---|
| Ingredients | % |
| TPO | 5 |
| HEMA | 45 |
| NC3050 | 50 |

The resultant film was cured as above and soak off results were obtained using the same methodology as above. The comparative results are reported in Table 2 below.

TABLE 2

| | Time Required For Soak Off With Precoat | |
|---|---|---|
| | Solvent | |
| Formula | Acetone | 50:50 Acetone:Methanol |
| 3 | >15 min | 9 min |

The present invention, therefore, is well adapted to carry out the objects and attain the ends and advantages mentioned, as well as others inherent therein. While the invention has been depicted and described and is defined by reference to particular embodiments of the invention, such references do not imply a limitation on the invention, and no such limitation is to be inferred. Consequently, the invention is intended to be limited only by the spirit and scope of the appended claims, giving full cognizance to equivalents in all respects.

What is claimed is:

1. A two package system comprising a first package comprising radiation polymerizable nail coating composition comprising a (meth)acrylic oligomer, (meth)acrylic polymer or (meth)acrylic monomer, or a mixture of a (meth)acrylic oligomer and/or (meth)acrylic polymer and a (meth)acrylic monomer, and a photoinitiator, wherein the oligomer or monomer has an acidic or basic ionizable group and a second package comprising a solvent system for removing the polymerizable nail coating composition after it has been applied to a nail and radiation cured, the solvent system comprising a hydroxyl-containing solvent and a non-hydroxyl-containing solvent wherein the hydroxyl-containing solvent is methanol and the non-hydroxyl-containing solvent is acetone.

2. The two package system of claim 1 wherein oligomer, polymer, or monomer has an acidic ionizable group selected from the group consisting of carboxylic acid, sulfonic acid, and phosphorous based acid.

* * * * *